US008039663B2

(12) United States Patent
Dershem

(10) Patent No.: US 8,039,663 B2
(45) Date of Patent: Oct. 18, 2011

(54) MONOMERS DERIVED FROM PENTACYCLOPENTADECANE DIMETHANOL

(75) Inventor: Stephen M. Dershem, San Diego, CA (US)

(73) Assignee: Designer Molecules, Inc., San Diego, CA (US)

( * ) Notice: Subject to any disclaimer, the term of this patent is extended or adjusted under 35 U.S.C. 154(b) by 767 days.

(21) Appl. No.: 12/100,332

(22) Filed: Apr. 9, 2008

(65) Prior Publication Data
US 2008/0257493 A1    Oct. 23, 2008

Related U.S. Application Data

(60) Provisional application No. 60/922,413, filed on Apr. 9, 2007.

(51) Int. Cl.
C07C 69/54 (2006.01)
C07C 69/56 (2006.01)
C07C 69/78 (2006.01)
C07C 229/28 (2006.01)
C07C 43/14 (2006.01)
C07C 43/16 (2006.01)
C07C 43/164 (2006.01)
C07C 43/166 (2006.01)

(52) U.S. Cl. ............ 560/194; 560/84; 560/43; 560/44; 560/125; 568/626; 568/659; 568/665

(58) Field of Classification Search .................. None
See application file for complete search history.

(56) References Cited

U.S. PATENT DOCUMENTS

| | | | |
|---|---|---|---|
| 4,540,829 A | 9/1985 | Hefner | |
| 4,774,267 A | 9/1988 | Weintraub | |
| 4,968,738 A | 11/1990 | Dershem | |
| 5,045,127 A | 9/1991 | Dershem et al. | |
| 5,064,480 A | 11/1991 | Dershem et al. | |
| 5,155,177 A | 10/1992 | Frihart | |
| 5,232,962 A | 8/1993 | Dershem et al. | |
| 5,306,333 A | 4/1994 | Dershem et al. | |
| 5,358,992 A | 10/1994 | Dershem et al. | |
| 5,376,721 A | 12/1994 | McGarry et al. | |
| 5,403,389 A | 4/1995 | Dershem | |
| 5,428,105 A | 6/1995 | McGarry et al. | |
| 5,430,112 A | 7/1995 | Sakata et al. | |
| 5,447,988 A | 9/1995 | Dershem et al. | |
| 5,489,641 A | 2/1996 | Dershem | |
| 5,567,761 A | 10/1996 | Song | |
| 5,596,669 A | 1/1997 | Murphy et al. | |
| 5,646,241 A | 7/1997 | Dershem et al. | |
| 5,707,782 A | 1/1998 | Economy et al. | |
| 5,717,034 A | 2/1998 | Dershem et al. | |
| 5,718,941 A | 2/1998 | Dershem et al. | |
| 5,753,748 A | 5/1998 | Dershem et al. | |
| 5,861,111 A | 1/1999 | Dershem et al. | |
| 5,880,170 A | 3/1999 | Imura et al. | |
| 5,969,036 A | 10/1999 | Dershem | |
| 5,973,166 A | 10/1999 | Mizori et al. | |
| 6,034,150 A | 3/2000 | Hoyle et al. | |
| 6,034,194 A | 3/2000 | Dershem | |
| 6,034,195 A | 3/2000 | Dershem | |
| 6,048,953 A | 4/2000 | Kawashimu et al. | |
| 6,121,358 A | 9/2000 | Dershem et al. | |
| 6,187,886 B1 | 2/2001 | Husson et al. | |
| 6,211,320 B1 | 4/2001 | Dershem et al. | |
| 6,300,456 B1 | 10/2001 | Musa | |
| 6,313,189 B1 | 11/2001 | Wenz et al. | |
| 6,369,124 B1 | 4/2002 | Hoyle et al. | |
| 6,423,780 B1 | 7/2002 | Dershem et al. | |
| 6,429,281 B1 | 8/2002 | Dershem et al. | |
| 6,521,731 B2 | 2/2003 | Dershem et al. | |
| 6,620,946 B2 | 9/2003 | Dershem et al. | |
| 6,743,852 B2 | 6/2004 | Dershem et al. | |
| 6,777,027 B2 | 8/2004 | Daly et al. | |
| 6,790,597 B2 | 9/2004 | Dershem | |
| 6,825,245 B2 | 11/2004 | Dershem | |
| 6,852,814 B2 | 2/2005 | Dershem et al. | |
| 6,855,745 B2 | 2/2005 | Hoyle et al. | |
| 6,916,856 B2 | 7/2005 | Dershem | |
| 6,946,523 B2 | 9/2005 | Dershem et al. | |
| 6,960,636 B2 | 11/2005 | Dershem et al. | |
| 6,963,001 B2 | 11/2005 | Dershem et al. | |
| 7,102,015 B2 | 9/2006 | Dershem et al. | |
| 7,157,587 B2 | 1/2007 | Mizori et al. | |
| 7,176,044 B2 | 2/2007 | Forray et al. | |
| 7,208,566 B2 | 4/2007 | Mizori et al. | |
| 7,230,055 B2 | 6/2007 | Musa | |
| 7,285,613 B2 | 10/2007 | Dershem et al. | |
| 7,309,724 B2 | 12/2007 | Dershem et al. | |
| 7,517,925 B2 | 4/2009 | Dershem et al. | |
| 7,678,879 B2 | 3/2010 | Dershem | |
| 2002/0062923 A1 | 5/2002 | Forray | |
| 2002/0099168 A1 | 7/2002 | Dershem et al. | |
| 2002/0188137 A1 | 12/2002 | Dershem et al. | |
| 2002/0193541 A1 | 12/2002 | Dershem et al. | |
| 2002/0198356 A1 | 12/2002 | Dershem et al. | |
| 2003/0008992 A1 | 1/2003 | Dershem et al. | |

(Continued)

FOREIGN PATENT DOCUMENTS

EP        1156036        11/2001

(Continued)

OTHER PUBLICATIONS

Andersson et al., "Initiator-Free Photopolymerization of an Aliphatic Vinyl Ether-Maleimide Monomer", *J Coatings Tech 69*: 1997, 91-95.

(Continued)

*Primary Examiner* — Daniel Sullivan
*Assistant Examiner* — Yevegeny Valenrod
(74) *Attorney, Agent, or Firm* — The Law Office of Jane K. Babin, Professional Corporation; Jane K. Babin

(57) ABSTRACT

The invention is based on the discovery that certain well-defined compounds derived from pentacyclopentadecane dimethanol are useful components in adhesive formulations. In particular, the invention compounds described herein provide high Tg values and low shrinkage. Compounds of the invention are useful as adhesives for use in the semiconductor packaging industry.

19 Claims, No Drawings

U.S. PATENT DOCUMENTS

| | | |
|---|---|---|
| 2003/0055121 A1 | 3/2003 | Dershem et al. |
| 2003/0060531 A1 | 3/2003 | Dershem et al. |
| 2003/0083436 A1 | 5/2003 | Deitch |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0129438 A1 | 7/2003 | Becker et al. |
| 2003/0208016 A1 | 11/2003 | Dershem et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0122168 A1 | 6/2004 | Murray |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0027082 A1 | 2/2005 | Narayan-Sarathy et al. |
| 2005/0136620 A1 | 6/2005 | Dershem et al. |
| 2005/0137277 A1 | 6/2005 | Dershem et al. |
| 2005/0267254 A1 | 12/2005 | Mizori et al. |
| 2005/0272888 A1 | 12/2005 | Dershem et al. |
| 2006/0009570 A1 | 1/2006 | Zychowski |
| 2006/0009578 A1 | 1/2006 | Dershem |
| 2006/0063014 A1 | 3/2006 | Forray |
| 2006/0069232 A1 | 3/2006 | Dershem |
| 2006/0142517 A1 | 6/2006 | Dershem |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dershem |
| 2008/0262191 A1 | 10/2008 | Mizori |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0041845 A1 | 2/2010 | Stephen et al. |
| 2010/0056671 A1 | 3/2010 | Dershem |
| 2010/0063184 A1 | 3/2010 | Dershem |

FOREIGN PATENT DOCUMENTS

| | | |
|---|---|---|
| JP | 2003002919 | 1/2003 |
| WO | WO-9406862 | 3/1994 |
| WO | WO 2004/099331 | 11/2004 |
| WO | WO-2005121190 | 12/2005 |
| WO | WO-2007100329 | 9/2007 |
| WO | WO-2008077141 | 6/2008 |
| WO | WO-2008124797 | 10/2008 |
| WO | WO-2008130894 | 10/2008 |
| WO | WO-2010019832 | 2/2010 |

OTHER PUBLICATIONS

Kohli et al., "Co-Polymerization of Maleimides and Vinyl Ethers: A Structural Study", *Macromolecules 31*: 1998, 5681-5689.

MONOMERS DERIVED FROM PENTACYCLOPENTADECANE DIMETHANOL

RELATED APPLICATIONS

This application claims the benefit of priority under 35. U.S.C. §119 of U.S. Provisional Application Ser. No. 60/922,413, filed Apr. 9, 2007, the disclosure of which is incorporated herein by reference in its entirety.

FIELD OF THE INVENTION

The present invention relates to thermosetting adhesive compositions, methods of preparation and uses therefor. In particular, the present invention relates to thermosetting compositions containing monomers derived from pentacyclopentadecane dimethanol (also known as pentacyclopentadecanedimethyol)

BACKGROUND OF THE INVENTION

As the electronics industry advances, and production of light weight components increases, the development of new materials gives producers increased options for further improving the performance and ease of manufacture of such components. Adhesive compositions are used for a variety of purposes in the fabrication and assembly of semiconductor packages and microelectronic devices. The more prominent uses include bonding of electronic elements such as integrated circuit (IC) chips to lead frames or other substrates, and bonding IC chips to other IC chips. Adhesives useful for electronic packaging applications typically exhibit properties such as good mechanical strength, curing properties that do not affect the component or the carrier, and rheological properties compatible with application to microelectronic and semiconductor components.

The microelectronics industry continues to require new adhesives that are able to meet its varying demands. Accordingly, there is a need for the development of materials to address the requirements of this rapidly evolving industry.

SUMMARY OF THE INVENTION

The invention is based on the discovery that certain compounds derived from pentacyclopentadecanedimethylol are useful components in adhesive compositions. The incorporation of dicyclopentadiene residues into unsaturated polyester resins has been reported in the art to reduce cure-induced shrinkage in certain thermosets. This effect is thought to arise from the inherently poor packing density of the polycyclic residues. Low shrinkage during cure is important for thermoset resins because this property results in coating and adhesive bonds with lower locked-in stress, which in turn are less likely to degrade in temperature cycling or corrosive environments. The polycyclic structure of dicyclopentadiene also imparts a higher glass transition to the final thermoset.

The backbone of the pentacyclopentadecanedimethylol starting material consists of five fused alicyclic rings as compared to three rings in dicyclopentadiene. The increase in fused cyclic structures within this molecule not only makes it a more hydrophobic building block, but also imparts superior glass transition temperatures and reduced cure shrinkage to its derivatives. In particular, the invention compounds described herein provide high Tg values and low shrinkage. This makes these compounds especially attractive as adhesives for use in the semiconductor packaging industry.

The thermosetting compounds of the present invention can be used in a variety of applications. Such applications would include, but are not limited to, matrix resins for fiber reinforced composites for marine, automotive, aerospace, civil engineering and sports equipment applications, adhesives and matrix resins for use in restorative dentistry, corrosion resistant coatings, and other commercial applications where low cure shrinkage and high temperature resistance is critical.

Specifically, the present invention provides compounds having the structure:

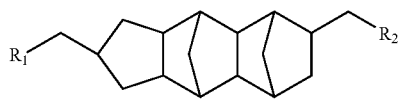

where $R_1$ and $R_2$ are each independently acrylate, methacrylate, styrenic, epoxy, oxetane, vinyl ether, mercaptopropionate, allyloxy, phenolic, aclyloxyphenyl, maleimide, citraconimide, or itaconimide. In certain embodiments, $R_1$ and $R_2$ are each independently selected from:

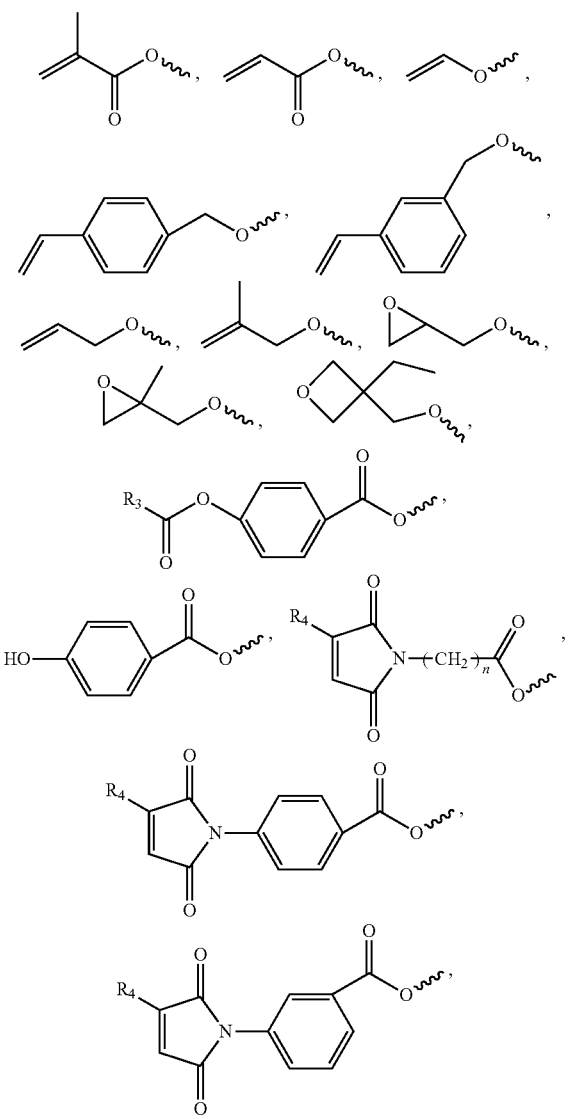

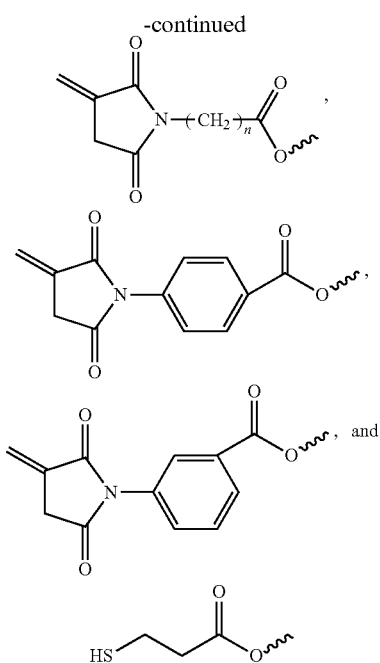

where n is 1 to 15, $R_3$ is $C_1$ to about $C_{20}$ alkyl, alkenyl or aryl; and $R_4$ is H, $C_1$ to about $C_6$ alkyl, or phenyl. In certain aspects, $R_3$ is $C_6$ to about $C_{12}$ alkyl, alkenyl or aryl. In other aspects, $R_4$ is H or methyl.

The invention also provide adhesive compositions that include at least one compound of the invention, and 0.1 to about 5 wt % of at least one curing initiator, based on the total weight of the composition. The at least one curing initiator can be a free radical initiator, such as a peroxide.

In other embodiments of the invention, the adhesive composition can include a photoinitiator, a thermal initiator or both a photoinitiator and a thermal initiator.

Also provided by the invention are adhesive compositions that are die-attach pastes, which may include 0.05 weight (wt %; percent based on total weight of the composition) to about 98 wt % of a compound of the invention; 0 to about 90 wt % of a filler; 0.1 wt % to about 5 wt % of at least one curing initiator; and 0.1 wt % to about 4 wt % of at least one coupling agent. The coupling agent can, for example, be a silicate ester, a metal acrylate salt, titanate, or a zirconate. The filler can be any filler, but may in certain embodiments be electrically conductive, thermally conductive or modifies rheology.

The present invention also provides assemblies that include a first article permanently adhered to a second article by a cured aliquot of the adhesive composition of the invention.

Also provided by the invention are methods for adhesively attaching a first article to a second article that include the steps of applying an adhesive composition of the invention to the first article, the second article or both the first article and the second article; contacting the first article and the second article, thereby forming an assembly, where the first article and the second article are separated only by the applied adhesive composition; and curing the applied adhesive composition, thereby adhesively attaching the first article to the second article.

The invention further provides methods for adhesively attaching a semiconductor device to a substrate that include the steps of applying an adhesive composition of the invention to the substrate, the semiconductor device or both the substrate and the semiconductor device; contacting the substrate and the semiconductor device, thereby forming an assembly, where the substrate and the semiconductor device are separated only by the applied adhesive composition; and curing the applied adhesive composition, thereby attaching the semiconductor device to the substrate. In certain embodiments, the semiconductor device is a die.

The invention also provides methods for adhesively attaching a semiconductor device to a substrate that include the steps of applying an adhesive composition of the invention to the substrate, the semiconductor device or both the substrate and the semiconductor device; melting the applied adhesive composition; contacting the semiconductor device and the substrate, such that the die and substrate are separated only by the applied adhesive composition; and curing the applied adhesive composition, thereby adhesively attaching the semiconductor device to the substrate. In certain embodiments of the method, the semiconductor device is a die.

In certain embodiments, invention adhesive compositions that include an invention compound have higher adhesion than a control composition derived from a corresponding compound containing fewer than five fused rings in the backbone. For example, the invention adhesive compositions may have at least about 20% or at least about 50% higher adhesion as compared to the control compositions.

DETAILED DESCRIPTION OF THE INVENTION

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, and formulation. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated).

DEFINITIONS

"About" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated).

As used herein, "aliphatic" refers to any alkyl, alkenyl, cycloalkyl, or cycloalkenyl moiety.

"Aromatic hydrocarbon," as used herein, refers to compounds having one or more benzene rings.

"Alkane," as used herein, refers to saturated straight-chain, branched or cyclic hydrocarbons having only single bonds. Alkanes have the general formula $C_nH_{2n+2}$.

"Cycloalkane," refers to an alkane having one or more rings in its structure.

As used herein, "alkyl" refers to straight or branched chain hydrocarbyl groups having from 1 up to about 100 carbon atoms. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —C(O)O—, —S—, —S(O)$_2$—, —OC(O)—O—, —NR—C(O)—, —NR—C(O)—NR—, —OC(O)—NR—, wherein R is H or lower alkyl, acyl, oxyacyl, carboxyl, carbamate, sulfonyl, sulfonamide, sulfuryl, and the like.

As used herein, "cycloalkyl" refers to cyclic ring-containing groups typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 6 up to about 14 carbon atoms and "substituted aryl" refers to aryl groups further bearing one or more substituents as set forth above.

As used herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above. The term heterocyclic is also intended to refer to heteroaromatic moieties.

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above.

As used herein, "alkylene" refers to a divalent alkyl moiety, and "oxyalkylene" refers to an alkylene moiety containing at least one oxygen atom instead of a methylene (CH$_2$) unit. "Substituted alkylene" and "substituted oxyalkylene" refer to alkylene and oxyalkylene groups further bearing one or more substituents as set forth above.

As used herein, "arylene" refers to a divalent aryl moiety. "Substituted arylene" refers to arylene moieties bearing one or more substituents as set forth above.

"Imide" as used herein, refers to a functional group having two carbonyl groups bound to a primary amine or ammonia. The general formula of an imide of the invention is:

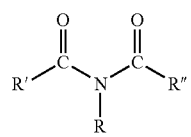

"Polyimides" are polymers of imide-containing monomers. Polyimides typically have one of two forms: linear or cyclic. Non-limiting examples of linear and cyclic (e.g. an aromatic heterocyclic polyimide) polyimides are shown below for illustrative purposes.

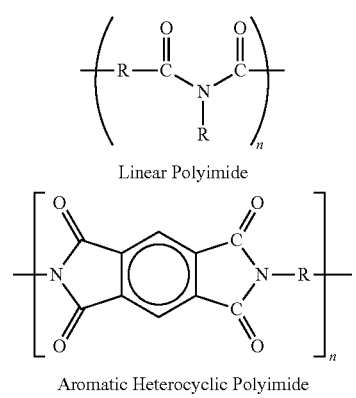

Linear Polyimide

Aromatic Heterocyclic Polyimide

"Maleimide," as used herein, refers to an N-substituted maleimide having the formula as shown below:

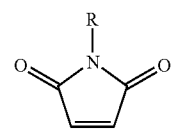

where the "R" group may be an aromatic, herteroaromatic, aliphatic, or polymeric moiety.

"Bismaleimide" or "BMI", as used herein, refers to a polyimide having the general structure shown below:

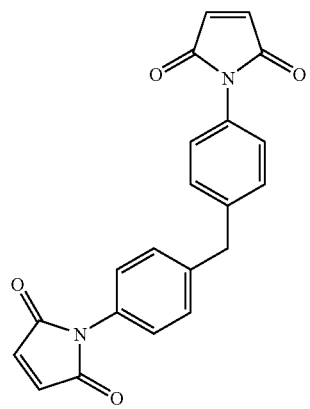

BMIs can cure through an addition rather than a condensation reaction, thus avoiding problems with volatiles forming. It can be produced by a vinyl-type polymerization of a pre-polymer terminated with two maleimide groups.

As used herein, the term "acrylate" refers to a compound bearing at least one moiety having the structure:

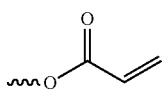

As used herein, the term "acrylamide" refers to a compound bearing at least one moiety having the structure:

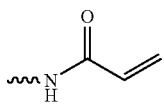

As used herein, the term "methacrylate" refers to a compound bearing at least one moiety having the structure:

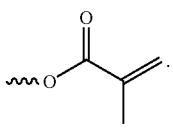

As used herein, the term "methacrylamide" refers to a compound bearing at least one moiety having the structure:

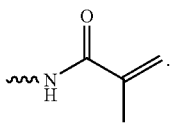

As used herein, the term "citraconimide" refers to a compound bearing at least one moiety having the structure:

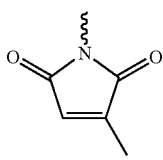

As used herein, the term "itaconimide" refers to a compound bearing at least one moiety having the structure:

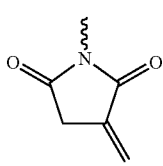

As used herein "epoxy" refers to a thermosetting epoxide polymer that cures by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof. Epoxies of the invention include compounds bearing at least one moiety having the structure:

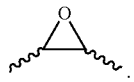

As used herein, the term "oxetane" refers to a compound bearing at least one moiety having the structure:

As used herein, the term "vinyl ether" refers to a compound bearing at least one moiety having the structure:

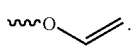

"Glass transition temperature" or "Tg": is used herein to refer to the temperature at which an amorphous solid, such as a polymer, becomes brittle on cooling, or soft on heating. More specifically, it defines a pseudo second order phase transition in which a supercooled melt yields, on cooling, a glassy structure and properties similar to those of crystalline materials e.g. of an isotropic solid material.

"Thermoplastic," as used herein, refers to the ability of a compound, composition or other material (e.g. a plastic) to melt to a liquid when heated, and freeze to solid, often brittle and glassy, state when cooled sufficiently.

"Thermoset," as used herein, refers to the ability of a compound, composition or other material to irreversibly "cure" to a stronger, harder form. Thermoset materials are typically polymers that may be cured, for example, through heat (e.g. above 200 degrees Celsius, or at lower temperatures in the presence of a suitable catalyst), via a chemical reaction (e.g. ring opening of epoxies, or chain extension of ethylenically unsaturated compounds), or through irradiation (e.g. U.V. irradiation).

Thermoset materials, such as thermoset polymers or resins, are typically liquid or malleable forms prior to curing, and therefore may be molded or shaped into their final form, and/or used as adhesives. Curing transforms the thermoset resin into a rigid infusible solid or rubber by a cross-linking process. Thus, energy and/or catalysts are added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

As used herein, "b-stageable" refers to the properties of an adhesive having a first solid phase followed by a tacky rubbery stage at elevated temperature, followed by yet another solid phase at an even higher temperature. The transition from the tacky rubbery stage to the second solid phase is thermosetting. However, prior to thermosetting, the material behaves similarly to a thermoplastic material. Thus, such adhesives allows for low lamination temperatures while providing high thermal stability.

Compounds Derived from Pentacyclopentadecane Dimethanol

The present invention provides compounds having the structure:

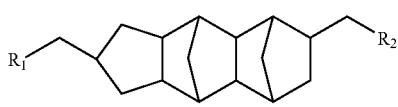

where $R_1$ and $R_2$ are each independently acrylate, methacrylate, styrenic, epoxy, oxetane, vinyl ether, mercaptopropionate, allyloxy, phenolic, aclyloxyphenyl, maleimide, citraconimide, or itaconimide.

Exemplary moieties contemplated for use as $R_1$ and $R_2$ include, but are not limited to the moieties set forth below:

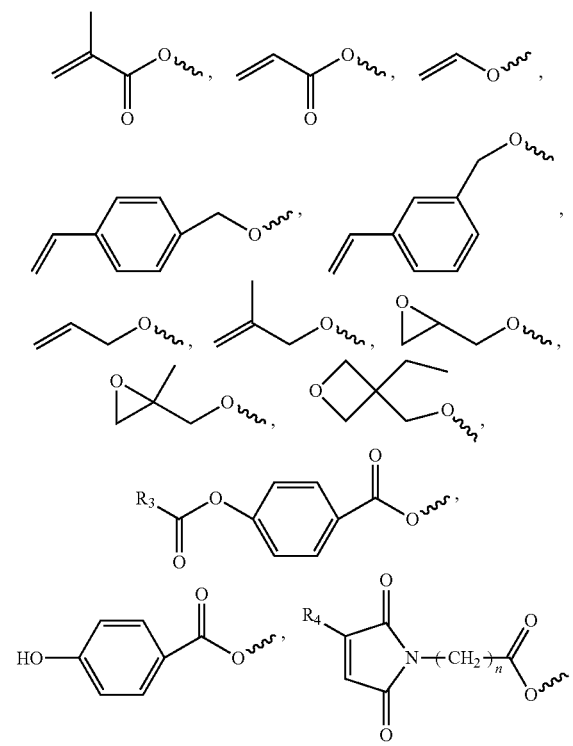

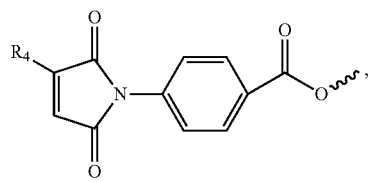

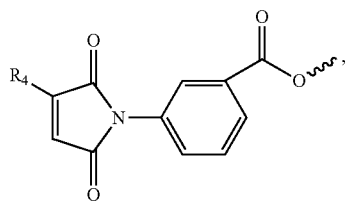

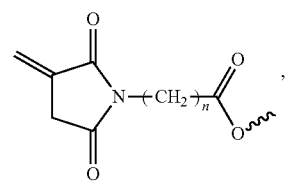

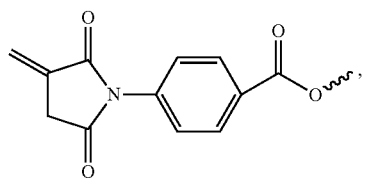

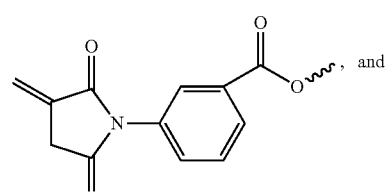

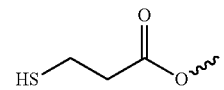

where n is 1 to 15, $R_3$ is $C_1$ to about $C_{20}$ alkyl, or aryl; and $R_4$ is H, $C_1$ to about $C_6$ alkyl, or phenyl.

Exemplary compounds contemplated in this invention include, but are not limited to the following representative structures:

C-1

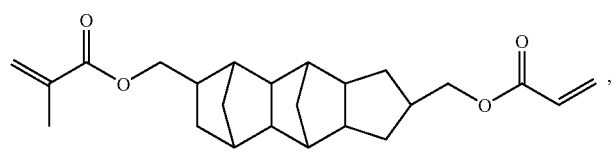

-continued

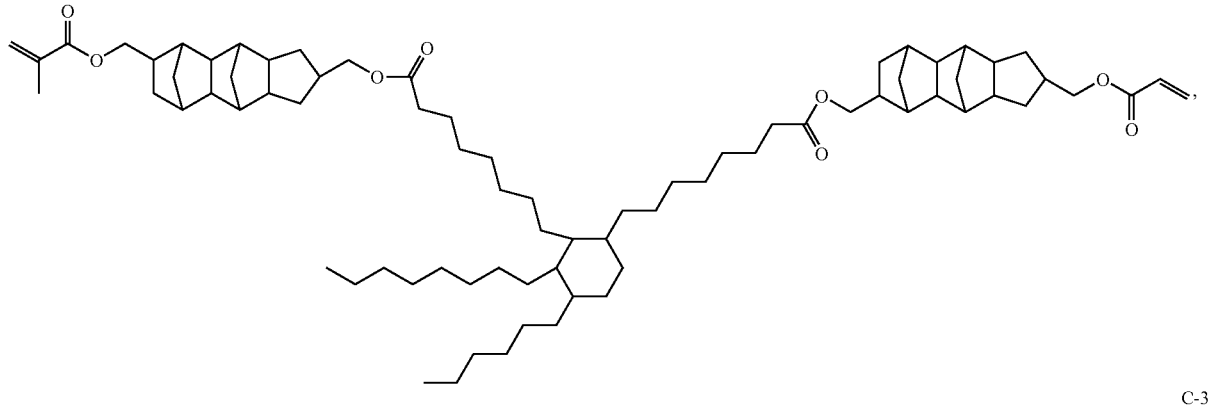
C-2

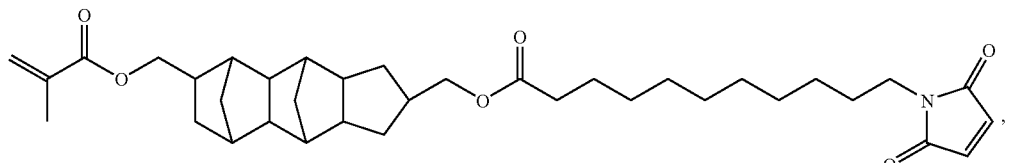
C-3

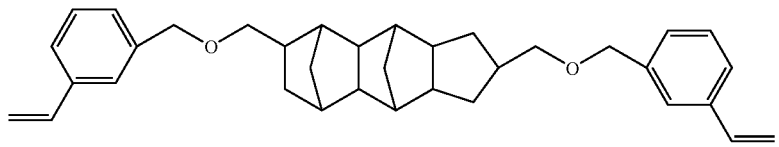
C-4

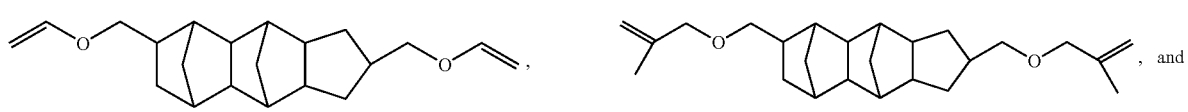
C-5   C-6

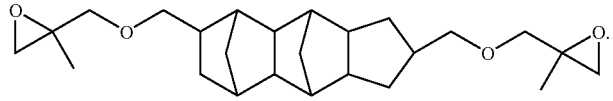

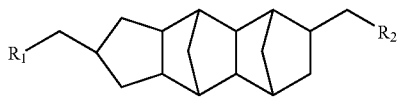
C-7

In certain embodiments, $R_3$ is $C_6$ to about $C_{12}$ alkyl, alkenyl or aryl. In other embodiments, $R_4$ is H or methyl.

Adhesive Compositions Containing Pentacyclopentadecane Dimethanol Derivatives

The invention also provides adhesive compositions that include at least one invention compound.

In certain embodiments, the adhesive composition of the invention includes: 0.05 weight percent (wt %; based on total weight of the composition) to about 98 wt %, of a compound having the structure:

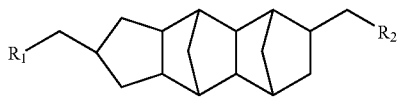

where $R_1$ and $R_2$ are each independently acrylate, methacrylate, styrenic, epoxy, oxetane, phenolic, mercapopropionate, maleimide, citraconimide, or itaconimide; 0 to about 90 wt % of a filler; 0.1 wt % to about 5 wt % of at least one curing initiator; and 0.1 wt % to about 4 wt %, of at least one coupling agent.

Advantageously, the adhesive compositions derived from pentacyclopentadecane dimethanol have increased adhesion as compared to adhesive compositions derived from corresponding control compounds containing fewer than five fused rings in the backbone, as demonstrated in EXAMPLE 7, below. In certain embodiments of the invention, the adhesion of the adhesive compositions of the invention is at least about 20% higher than the control. In other embodiments, increased adhesion is at least about 50% higher than the control. In yet further embodiments, increased adhesion is at least about 100% higher than the control.

Curing Initiators. In some embodiments, the adhesive compositions contain at least one curing initiator, which is present in the composition from 0.1 wt % to about 5 wt %. In some embodiments, the curing initiator is a free-radical initiator. As used herein, the term "free radical initiator" refers to any chemical species which, upon exposure to sufficient energy (e.g., light, heat, or the like), decomposes into two parts which are uncharged, but which each posses at least one unpaired electron. Free radical initiators suitable for use in the practice of the present invention are compounds which decompose with a half life in the range of about 10 hours at temperatures in the range of about 70° C. up to 180° C. Exemplary free radical initiators include, but are not limited to, peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis (tert-butyl peroxyisopropyl)benzene, and tert-butyl hydroperoxide).

Photoinitiators. The term "free radical initiator" also includes photoinitiators. Curing of adhesive compositions of the invention that contain a photoinitiator can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive composition.

In a further embodiment, the adhesive compositions of the present invention are die-attach pastes.

The adhesives and die-attach paste adhesives described herein may further contain additional compounds. Such compounds include, for example, epoxies (such as phenolics, phenolic novolacs and cresolic novolacs), imides, monomaleimides, bismaleimides, polymaleimides, cyanate esters, vinyl ethers, vinyl esters, vinyl acetates, olefins, cyanoacrylates, styrenics, oxazolines, benzoxazines, oxetanes, and combinations thereof.

Fillers. In some embodiments, fillers are contemplated for use in the practice of the present invention, which can be electrically conductive and/or thermally conductive, and/or fillers which act primarily to modify the rheology or coefficient of expansion of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds, which act primarily to modify rheology or coefficient of expansion, include silica, fumed silica, fumed alumina, fumed titanium dioxide, calcium carbonate, and the like.

Coupling Agents. As used herein, the term "coupling agent" refers to chemical species that are capable of bonding to a mineral surface and which also contain polymerizably reactive functional group(s) so as to enable interaction with the adhesive composition such as a die-attach paste. Coupling agents thus facilitate linkage of the adhesive composition to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates, or compounds that contain a copolymerizable group and a chelating ligand (e.g., phosphine, mercaptan, acetoacetate, and the like). In some embodiments, the coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste. In certain embodiments coupling agents contemplated for use in the practice of the invention are oligomeric silicate coupling agents such as poly(methoxyvinylsiloxane).

In general, the adhesive compositions will cure within a temperature range of about 80° C. to about 220° C., and curing will be effected within a period of time of less than 1 minute to 60 minutes. As will be understood by those skilled in the art, the time and temperature curing profile for each adhesive composition will vary, and different compositions can be designed to provide the curing profile that will be suited to the particular industrial manufacturing process.

Additional Compounds. In certain embodiments, the adhesive compositions of the invention, such as die-attach pastes, may contain modifiers that lend additional flexibility and toughness to the resultant cured adhesive. Such modifiers may be thermoset or thermoplastic materials having a Tg of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol. When present, toughening compounds may be included at an amount up to about 15 percent by weight of the maleimide and other monofunctional vinyl compound.

Inhibitors for free-radical cure may also be added to the adhesive compositions and die-attach pastes described herein to extend the useful shelf life. Examples of free-radical inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful inhibitors include hydrogen-donating antioxidants, such as derivatives of p-phenylenediamine and diphenylamine. It is also well know in the art that hydrogen-donating antioxidants may be synergistically combined with quinones, and metal deactivators to make a very efficient inhibitor package. Examples of suitable quinones include benzoquinone; 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine. Nitroxyl radical compounds such as TEMPO (2,2, 6,6-tetramethyl-1-piperidnyloxy, free radical) are also effective as inhibitors at low concentrations. The total amount of antioxidant plus synergists typically falls in the range of about 100 to about 2000 ppm relative to the weight of total base resin. Other additives, such as adhesion promoters, in types and amounts known in the art, may also be added.

The adhesive compositions, such as die-attach paste adhesives, described herein will generally perform within commercially acceptable ranges for die attach adhesives. Commercially acceptable values for die shear for the adhesives on a 80×80 mil$^2$ silicon die are typically in the range of greater than or equal to 1 kg at room temperature, and greater than or equal to 0.5 kg at 260° C.

Assemblies

In yet another embodiment of the invention, assemblies of components adhered together by the above-described adhesive compositions and/or adhesive die attach pastes are provided. Thus, for example, assemblies having a first article adhered to a second article by a cured aliquot of an adhesive composition containing at least one monomer of the invention are provided. Articles contemplated for assembly employing invention adhesives include electronic components such as dies, memory devices, ASIC devices, microprocessors, flash memory devices, and the like. Also encompassed by the invention are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

Additional embodiments of the invention include adhesive bonded structures containing at least one compound described herein. Non-limiting examples of the adhesive bonded structures include electronic components bonded to a substrate, and circuit components bonded to printed wire boards. In other embodiments of the invention, articles of manufactures can be comprised substantially of a cured amount of the composition described herein, such as an industrial, marine, automotive, airline, aerospace, sporting goods, medical or dental article. Such articles of manufacture can also include fillers, extenders, pigments and/or reinforcing materials along with the compositions disclosed herein.

Methods of Using Pentacyclopentadecane Dimethanol Derivative Compounds and Compositions According to the present invention, methods for adhesively attaching a first article to a second article. Such methods can be performed, for example, by (a) applying an adhesive composition of the invention to the first article, the second article or both the first article and the second article; (b) contacting the first article and the second article to form an assembly where the first article and the second article are separated only by the applied adhesive composition; and (c) curing the applied adhesive composition, thereby attaching the first article to the second article.

In certain embodiments, the invention provides methods for adhesively attaching a semiconductor device, such as a die, to a substrate by (a) applying an adhesive composition of the invention to the substrate, the semiconductor device or both the substrate and the semiconductor device; (b) contacting the substrate and the semiconductor device to form an assembly, where the substrate and the electronic component are separated only by the applied adhesive composition; and (c) curing the applied adhesive composition, thereby attaching the semiconductor device to the substrate In still further embodiments, the invention provided b-stageable type methods for adhesively attaching a semiconductor die to a substrate. Such methods can be performed, for example, by (a) applying an invention adhesive composition to the substrate, the semiconductor device or both the substrate and the semiconductor device; (b) melting the adhesive composition applied in step (a); (c) contacting the semiconductor device and the substrate, such that the die and substrate are separated only by the applied adhesive composition; and (d) curing the applied adhesive composition, thereby attaching the semiconductor device to the substrate.

Conditions suitable to cure invention adhesives include subjecting the above-described assemblies to a temperature of less than about 200° C. for about 0.5 up to about 2 minutes. This rapid, short duration heating can be accomplished in a variety of ways, e.g., with an in-line heated rail, a belt furnace, or the like. Optionally, the material can be oven cured at about 150° C. to about 220° C.

It will be understood by the skilled artisan that using the compounds and methods of the present invention, it is possible to prepare adhesives having a wide range of cross-link densities by the judicious choice and amount of mono-, bis- or polyfunctional compounds. The greater proportion of poly-functional compounds reacted, the greater the cross-link density. If thermoplastic properties are desired, the adhesive compositions can be prepared from, or contain a higher percentage of, mono-functional compounds to limit the cross-link density. A minor amount of poly-functional compound can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

The invention will now be further described with reference to the following non-limiting examples.

EXAMPLES

It should be noted that for each of the following exemplary compounds, where the substitution on the pentacyclopenta-decane backbone is asymmetric or where the molecule has been extended with another bi-functional reactant, that only a single representative structure is shown. That is to say, such compounds are in fact composed of statistical distributions of several molecules. Only the most predominant species in these distributions are shown.

Example 1

Preparation of Compound C-1

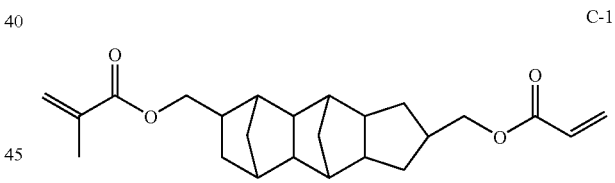

C-1

A two-neck, 500 mL flask was charged with 26.24 g (0.1 mole) pentacyclopentadecane dimethanol (Celanese Corp., Dallas, Tex.), 7.93 g (0.11 mole) acrylic acid, 9.47 g (0.11 mole) methacrylic acid, 250 mL toluene, 1.5 g methane-sulfonic acid, and 80 mg 4-methoxyphenol. A magnetic stir bar was placed in the flask and a Dean-Stark trap and condenser were attached. The mix was refluxed under an air sparge for three hours and 3.5 mL water (3.6 mL theoretical yield) was collected in the trap. The mixture was cooled to room temperature and neutralized with a mix of 20 g sodium bicarbonate and 4 mL water. The mix was dried with 10 g anhydrous magnesium sulfate and then passed over 25 g of silica gel. The bulk of the toluene was removed under vacuum on a rotary evaporator. The last trace of solvent was removed using an air sparge. The final product was an amber liquid that had a 25° C. viscosity of 5,080 centipoise. The product weighed 35.9 g (93.4% of theoretical yield). Thermogravimetric analysis (TGA) was performed on the compound (ramp rate of 10° C. per minute in air) and the retained weight was 99.2% and 98.7% at 200° C. and 300° C., respectively.

The decomposition onset was 428° C. An FTIR was run on this compound and significant absorptions were found at 2943, 1721, 1637, 1452, 1406, 1294, 1162, 1054, 982, and 810 wavenumbers.

Example 2

Preparation of Compound C-2

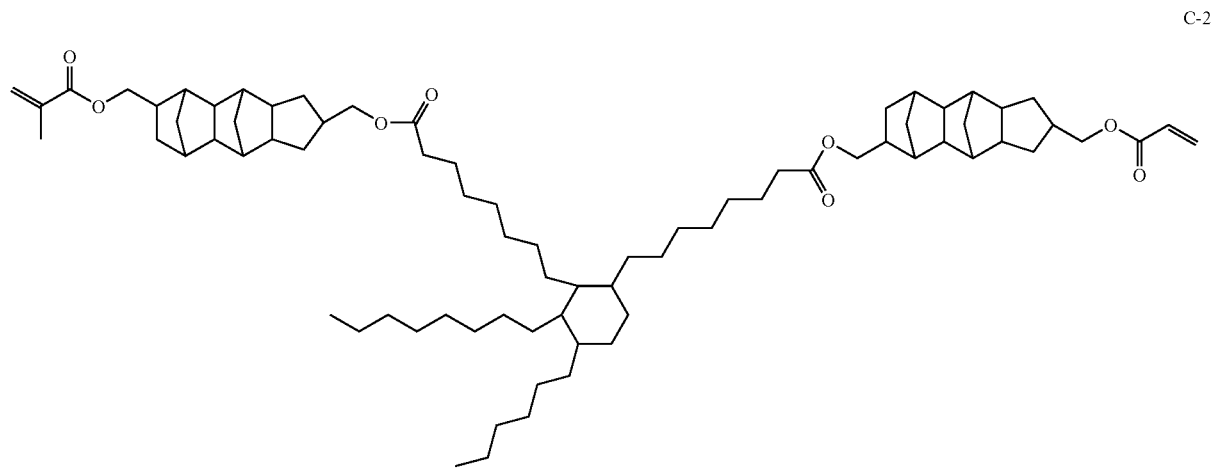

C-2

A two-neck, one liter flask was charged with 63.0 g (0.24 mole) pentacyclopentadecane dimethanol (PCPD-DM), 56.5 g (0.1 mole) Empol 1008 hydrogenated dimer acid (Cognis Corporation, Cincinnati, Ohio), 400 mL toluene, and 4.0 g methanesulfonic acid. The flask was equipped as in EXAMPLE 1 and the mix was refluxed for 40 minutes to collect 3.8 mL (3.6 mL expected). The flask was cooled and then 11.53 g (0.16 mole) acrylic acid, 13.77 g (0.16 mole) methacrylic acid, and 106 mg 4-methoxyphenol were added and a second reflux was conducted for three hours under an air sparge. Work-up similar to EXAMPLE 1 gave 122.8 g of a clear, red, viscous liquid. The 5 rpm viscosity at 25° C. was 80,267 centipoise. The product had significant absorptions at 2928, 2854, 1726, 1637, 1464, 1406, 1294, 1166, 983, and 810 wavenumbers.

Example 3

Preparation of Compound C-3

A two-neck, 500 mL flask was charged with 26.24 g (0.1 mole) pentacyclopentadecane dimethanol, 9.04 g (0.105 mole) methacrylic acid, 29.54 g (0.105 mole) maleimidoundecanoic acid, 150 mL toluene, 2.0 g methanesulfonic acid, and 60 mg hydroquinone. A magnetic stir bar was placed in the flask and a gas inlet tube, Dean-Stark trap and condenser were attached. The mix was refluxed under an air sparge for 3.5 hours and 3.7 mL water (3.6 mL theoretical yield) was collected in the trap. The mixture was cooled to room temperature and neutralized with a mix of 15 g sodium bicarbonate and 5 mL water. The mix was dried with 12 g anhydrous magnesium sulfate and then passed over 20 g of silica gel. The bulk of the toluene was removed under vacuum on a rotary evaporator. The last trace of solvent was removed using an air sparge. The final product was a viscous, clear, red liquid that had a 40° C. viscosity of 3,028 centipoise. The product weighed 55.12 g (92.8% of theoretical yield). Thermogravimetric analysis (TGA) was performed on the compound (ramp rate of 10° C. per minute in air) and the retained weight was 100.0% and 99.9% at 200° C. and 300° C., respectively. The decomposition onset was 432.8° C. An FTIR was run on this compound and significant absorptions were found at 2925, 1714, 1638, 1407, 1172, 827, and 695 wavenumbers.

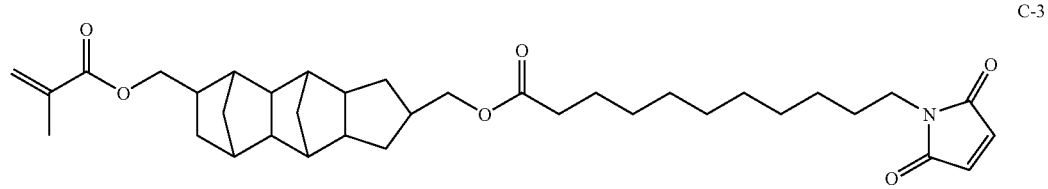

C-3

Example 4

Preparation of Compound C-4

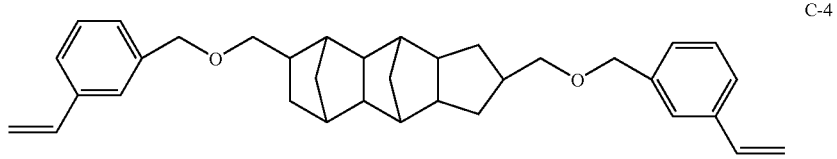

C-4

A one-neck, 500 mL flask was charged with 26.24 g (0.1 mole) pentacyclopentadecane dimethanol, 33.58 g (0.22 mole) vinylbenzylchloride, and 50 mL toluene. The flask was heated and swirled to obtain a homogeneous solution. The flask was then charged with 1.5 g tetrabutylammonium bromide, and 12.0 g (0.3 mole) sodium hydroxide. A magnetic stir bar was placed in the flask and the mixture was stirred and heated at 45° C. for 22.75 hours. The mix was diluted with 50 mL toluene and then extracted with 50 mL deionized water followed by 50 mL brine. The toluene solution was dried with 20 g magnesium sulfate and then passed over 20 g silica gel. The bulk of the toluene was removed under vacuum on a rotary evaporator. The last trace of solvent was removed using an air sparge. The final product was a viscous light yellow liquid. The product weighed 17.8 g (36% of theoretical yield). Thermogravimetric analysis (TGA) was performed on the compound (ramp rate of 10° C. per minute in air) and the retained weight was 99.94% and 99.24% at 200° C. and 300° C., respectively. The decomposition onset was 411° C. An FTIR was run on this compound and significant absorptions were found at 2939, 2857, 1630, 1356, 1085, 988, 904, 795 and 713 wavenumbers.

Example 5

Preparation of Compound C-5

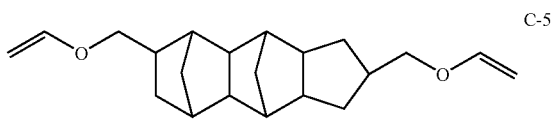

C-5

A one-neck, 500 mL flask was charged with 26.24 g (0.1 mole) pentacyclopentadecane dimethanol, 100 g (1.0 mole) butyl vinyl ether (BVE), and 0.2 g of catalyst (palladium acetate-1,10-phenanthroline complex). The flask was attached to a rotary evaporator and then stirred overnight at 60° C. The mix had become a homogeneous, red solution by the next morning. The bath temperature was reduced to 45° C. and then the excess BVE was removed under aspirator vacuum. The crude BVE was recycled for the next equilibrium exchange. The bath temperature was again raised to 60° C. and then the 1-butanol co-product was sparged off using clean dry air. The flask was then charged with another 100 g BVE (recycled plus some fresh make-up BVE) and the equilibrium transvinylation exchange was continued for another two hours by rotating the mix again in the water bath at 60° C. This cycle was repeated a total of five times. All of the volatiles were then removed and the product was diluted with 100 mL heptane and this solution was then passed over 10 g of silica gel. The heptane was removed to yield 27.87 g (88.7% of theory) of a clear, orange liquid. The divinyl ether compound had a 25° C. viscosity of 1,081 centipoise at 5 rpm. Thermogravimetric analysis (TGA) was performed on the compound (ramp rate of 10° C. per minute in air) and the retained weight was 100.0% and 98.18% at 100° C. and 200° C., respectively. An FTIR was run on this compound and significant absorptions were found at 2945, 1634, 1609, 1470, 1317, 1198, 1072, 992, and 808 wavenumbers.

Example 6

Preparation of Compound C-6

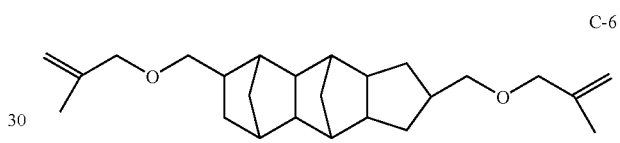

C-6

A one-neck, 250 mL flask was charged with 52.48 g (0.2 mole) pentacyclopentadecane dimethanol, 40.75 g (0.45 mole) 2-methyl-3-chloropropene, and 50 mL toluene. The flask was heated and swirled to obtain a homogeneous solution. The flask was then charged with 2.0 g tetrabutylammonium bromide, and 24.0 g (0.6 mole) sodium hydroxide. A magnetic stir bar was placed in the flask and the mixture was stirred and heated at 50° C. for 36 hours. An FTIR revealed that some alcohol functionality still remained so another 4.65 g (0.05 mole) 2-methyl-3-chloropropene was added and the reaction was continued for another 16 hours. The mixture was the diluted with 100 mL toluene and then extracted with 3×50 mL deionized water followed by 50 mL brine. The toluene solution was dried with 15 g magnesium sulfate and then passed over 25 g silica gel. The bulk of the toluene was removed under vacuum on a rotary evaporator. The last trace of solvent was removed using an air sparge. The final product was a nearly colorless, and fairly low viscosity (246 centipoise at 25° C.), liquid. The product weighed 71.54 g (or 96.5% of theoretical yield). Thermogravimetric analysis (TGA) was performed on the compound (ramp rate of 10° C. per minute in air) and the retained weight was 100.0% and 98.44% at 100° C. and 200° C., respectively. An FTIR was run on this compound and significant absorptions were found at 2943, 2856, 1655, 1450, 1372, 1253, 1099, 980 and 895 wavenumbers.

Example 7

Performance of Pentacyclopentadecane Dimethanol Monomers

A comparative example compound (CE-1) was prepared that was analogous to compound C-2 where the pentacyclopentadecane dimethanol was replaced with tricyclodecane dimethanol. All ratios of other reagents used were identical to those used to produce the C-2 monomer.

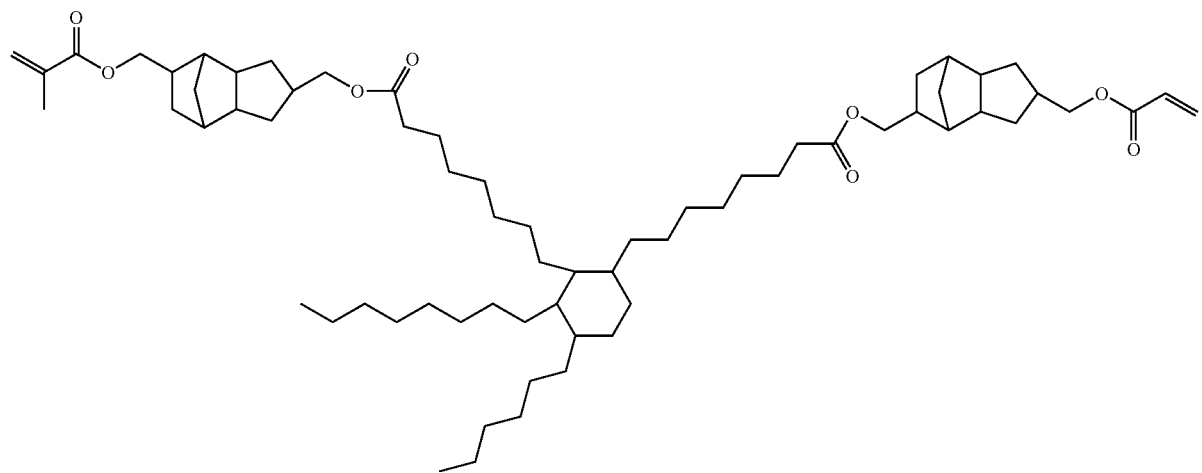

CE-1

Test portions of the C-2 and CE-1 monomers were catalyzed with two-weight percent dicumyl peroxide. These mixtures were used to affix aluminum studs (177 mil head diameter; parts numbered 1-7 in Table 1, below) to both copper and steel slugs. These assemblies were cured in an oven at 185° C. for 45 minutes. Room temperature tensile adhesion was then using a Sebastian III tensile tester. The results of these tests are summarized in Table 1.

TABLE 1

Tensile Adhesion (pounds force) Comparison of Compounds C-2 and CE-1

| Part Number | Compound C-2 | | Compound CE-1 | |
|---|---|---|---|---|
| | Copper | Steel | Copper | Steel |
| 1 | 55 | 90 | 14 | 41 |
| 2 | 44 | 99 | 34 | 3 |
| 3 | 66 | 76 | 35 | 49 |
| 4 | 44 | 59 | 37 | 71 |
| 5 | 50 | 28 | 45 | 62 |
| 6 | 35 | 98 | 28 | 42 |
| 7 | 39 | 71 | 32 | 70 |
| Average - | 45.6 | 74.4 | 30.7 | 48.3 |
| $\sigma_{n-1}$ - | 10.5 | 25.2 | 10.0 | 23.5 |

The invention compound C-2 had approximately fifty percent higher adhesion than the CE-1 control on both copper and steel. However, the adhesion standard deviation was approximately the same for both samples. The performance of the pentacyclopentadecane dimethanol based compound was therefore superior to an analogous compound based on the tricyclodecane dimethanol.

While the invention has been described with respect to these specific examples, it should be clear that other modifications and variations would be possible without departing from the spirit of this invention.

What is claimed is:

1. A compound having the structure:

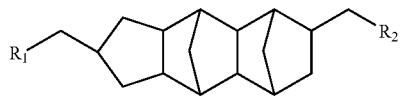

wherein:

each of $R_1$ and $R_2$ is independently selected from the group consisting of acrylate, methacrylate, styrenic, epoxy, oxetane, vinyl ether, mercaptopropionate, allyloxy, phenolic, aclyloxyphenyl, maleimide, citraconimide, and itaconimide.

2. The compound of claim 1, wherein each of $R_1$ and $R_2$ is independently selected from the group consisting of:

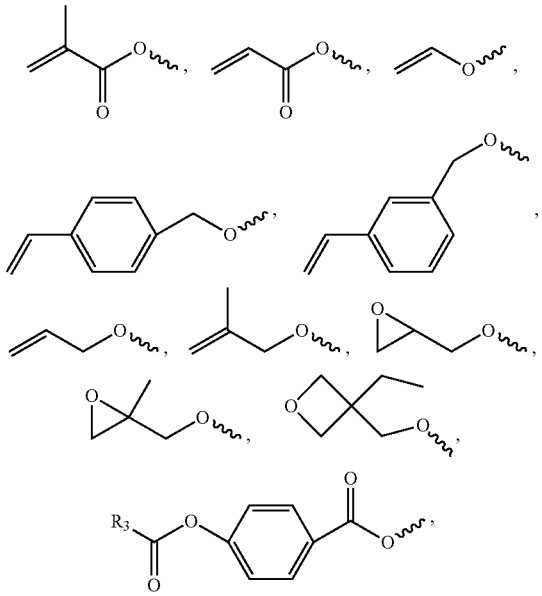

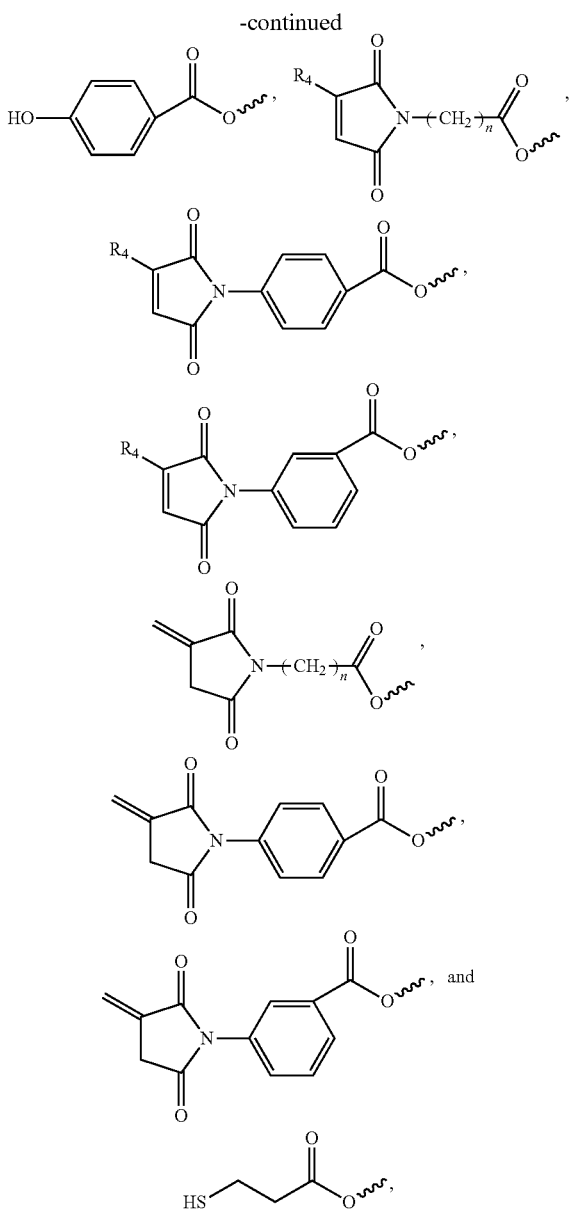

wherein:

n is 1 to 15;

$R_3$ is $C_1$ to about $C_{20}$ alkyl, alkenyl or aryl; and $R_4$ is H, $C_1$ to about $C_6$ alkyl, or phenyl.

3. The compound of claim 1, wherein $R_3$ is $C_6$ to about $C_{12}$ alkyl, alkenyl or aryl.

4. The compound of claim 1, wherein $R_4$ is H or methyl.

5. An adhesive composition comprising:
(a) at least one compound of claim 1; and
(b) 0.1 to about 5 wt % of at least one curing initiator, based on the total weight of the composition.

6. The adhesive composition of claim 5, wherein the at least one curing initiator is a free radical initiator.

7. The adhesive composition of claim 5, wherein the at least one curing initiator is a peroxide.

8. The adhesive composition of claim 5, further comprising a phototoinitiator, a thermal initiator or both a phototoinitiator and a thermal initiator.

9. An adhesive composition comprising:
(a) 0.05 weight percent based on total weight of the composition (wt %) to about 98 wt % of the compound of claim 1;
(b) 0 to about 90 wt % of a filler;
(c) 0.1 wt % to about 5 wt % of at least one curing initiator;
(d) 0.1 wt % to about 4 wt %, of at least one coupling agent, wherein the adhesive composition is a die-attach paste.

10. The adhesive composition of claim 9, wherein the coupling agent is a silicate ester, a metal acrylate salt, titanate, or a zirconate.

11. The adhesive composition of claim 9, wherein the filler is electrically conductive, thermally conductive or modifies rheology.

12. A method for adhesively attaching a first article to a second article, comprising:
(a) applying the adhesive composition of claim 5 to the first article, the second article or both the first article and the second article;
(b) contacting the first article and the second article, thereby forming an assembly, wherein the first article and the second article are separated only by the adhesive composition applied in step (a); and
(c) curing the adhesive composition applied in step (a), thereby adhesively attaching the first article to the second article.

13. A method for adhesively attaching a semiconductor device to a substrate comprising:
(a) applying the adhesive composition of claim 5 to the substrate, the semiconductor device or both the substrate and the semiconductor device;
(b) contacting the substrate and the semiconductor device, thereby forming an assembly, wherein the substrate and the semiconductor device are separated only by the adhesive composition applied in step (a); and
(c) curing the adhesive composition applied in step (a), thereby attaching the semiconductor device to the substrate.

14. The method of claim 13, wherein the semiconductor device is a die.

15. A method for adhesively attaching a semiconductor device to a substrate comprising:
(a) applying the adhesive composition of claim 5 to the substrate, the semiconductor device or both the substrate and the semiconductor device;
(b) melting the adhesive composition applied in step (a);
(c) contacting the semiconductor device and the substrate, wherein the die and substrate are separated only by the adhesive composition applied in step (a); and
(d) curing the adhesive composition applied in step (a), thereby adhesively attaching the semiconductor device to the substrate.

16. The method of claim 15, wherein the semiconductor device is a die.

17. An adhesive composition comprising the compound of claim 1, wherein the composition has higher adhesion than a control composition derived from a corresponding compound containing fewer than five fused rings in the backbone.

18. The adhesive composition of claim 17, wherein the higher adhesion is at least about 50% increase in adhesion as compared to the control composition.

19. The adhesive composition of claim 17, wherein the higher adhesion is at least about 20% increase in adhesion as compared to the control composition.

* * * * *